(12) United States Patent
Morad et al.

(10) Patent No.: US 11,769,363 B1
(45) Date of Patent: Sep. 26, 2023

(54) FEMININE HYGIENE PRODUCT DISPENSER WITH TRIGGER

(71) Applicant: The Tranzonic Companies, Cleveland, OH (US)

(72) Inventors: Fred I. Morad, Toluca Lake, CA (US); Robert A. Acosta, Norwalk, CA (US)

(73) Assignee: THE TRANZONIC COMPANIES, Cleveland, OH (US)

( * ) Notice: Subject to any disclaimer, the term of this patent is extended or adjusted under 35 U.S.C. 154(b) by 0 days.

(21) Appl. No.: 17/977,485

(22) Filed: Oct. 31, 2022

(51) Int. Cl.
| | |
|---|---|
| *G07F 11/20* | (2006.01) |
| *A61F 15/00* | (2006.01) |
| *G07F 9/02* | (2006.01) |
| *G07F 17/00* | (2006.01) |

(52) U.S. Cl.
CPC ............ *G07F 11/20* (2013.01); *A61F 15/001* (2013.01); *G07F 9/023* (2013.01); *G07F 17/0014* (2013.01)

(58) Field of Classification Search
CPC .............................. A61F 15/001; G07F 11/22
USPC ..................................................... 221/15, 16
See application file for complete search history.

(56) References Cited

U.S. PATENT DOCUMENTS

| | | | | | |
|---|---|---|---|---|---|
| 2,193,759 | A | * | 3/1940 | Birr ..................... | A47K 10/3643 225/8 |
| 2,391,851 | A | * | 12/1945 | Willard ................ | A63B 71/148 2/2 |
| 2,562,786 | A | * | 7/1951 | Hitchcock ............... | G05G 15/04 192/33 R |
| 2,889,251 | A | * | 6/1959 | Gross ...................... | A61K 31/70 530/320 |
| 3,459,343 | A | * | 8/1969 | Rasmussen ............... | A47K 5/10 222/88 |
| 4,579,398 | A | * | 4/1986 | Golby ..................... | A47K 10/28 312/34.15 |
| 10,192,386 | B2 | * | 1/2019 | Morad ................. | G07F 11/1657 |
| 11,200,772 | B2 | | 12/2021 | Morad et al. | |
| 2005/0263545 | A1 | * | 12/2005 | Ophardt ................ | G01F 11/025 222/181.3 |

* cited by examiner

*Primary Examiner* — Timothy R Waggoner
(74) *Attorney, Agent, or Firm* — Taft Stettinius & Hollister LLP; Ryan O. White; Daniel J. Krieger (57) ABSTRACT

A feminine hygiene product dispenser for dispensing feminine hygiene products. The dispenser includes a rack to hold the feminine hygiene products. A weight is adapted to fit within the rack, wherein the weight is supported by a last feminine hygiene product to be dispensed from the rack, the weight including an indicator. A housing includes a door, wherein the door has a window through which the indicator appears in the absence the plurality of feminine hygiene products. A product dispensing module includes a suction cup, a delivery tray, and a trigger operatively connected to the suction cup and to the delivery tray, wherein actuation of the trigger moves the suction cup to a holding position and positions the delivery tray to a product delivery position. The trigger slides freely when the suction cup is in the holding position to prevent the delivery tray from dispensing one of the feminine hygiene products.

20 Claims, 6 Drawing Sheets

FEMININE HYGIENE PRODUCT DISPENSER WITH TRIGGER

FIELD OF THE DISCLOSURE

The present disclosure relates to a vending machine that dispenses hygiene products. More specifically, the present disclosure relates to a vending machine that dispenses feminine hygiene products in response to activation of a trigger.

BACKGROUND OF THE DISCLOSURE

Different types of vending machines dispense hygiene products in response to a buyer depositing money at the machine, such as coinage or paper bills. Other types of vending machines dispense hygiene products in response to activation of a contact or non-contact sensor without the need to deposit any type of money. Such machines are often located in the restrooms of public or corporate buildings to dispense feminine hygiene products. The owners or proprietors of such facilities provide the feminine hygiene products without remuneration, since such products are considered to be essential and, as such, are provided free of charge.

In some facilities, where these hygiene product dispensers are located in low traffic areas, the dispensing machine does not require a large storage area for storing products. For instance, smaller restaurants and smaller schools do not require large capacity feminine hygiene product dispensers due to a lower demand for the products. Consequently, these types of reduced traffic facilities are not interested in purchasing large capacity dispensers due to the higher cost associated with such dispensers. What is needed therefore, is a hygiene product dispenser having a lower capacity that can be easily filled, but which still reduces the likelihood of an individual removing more products than is necessary.

SUMMARY

In one embodiment, there is provided a feminine hygiene product dispenser including a rack to hold a plurality of feminine hygiene products and a weight adapted to fit within the rack. The weight is supported by a last feminine hygiene product to be dispensed from the rack, wherein the weight includes an indicator. A housing includes a door, wherein the door includes a window through which the indicator appears in the absence the plurality of feminine hygiene products. A product dispensing module includes a suction cup, a delivery tray, and a trigger operatively connected to the suction cup and to the delivery tray. Actuation of the trigger moves the suction cup to a holding position and positions the delivery tray to a product delivery position.

In some embodiments, the feminine hygiene product dispenser further includes a linkage operatively connected to the trigger, to the suction cup, and to the delivery tray, wherein actuation of the trigger moves the linkage to engage the suction cup into contact with a timing plate at the holding position.

In some embodiments, the feminine hygiene product dispenser further includes a trigger plate fixedly coupled to the trigger and to a lever housing, wherein the lever housing supports sliding movement of the trigger plate.

In some embodiments, the feminine hygiene product dispenser includes wherein the trigger plate includes a tab that engages a slot of the lever housing, wherein the slot incudes terminating ends that limit movement of the trigger plate and the trigger.

In some embodiments, the feminine hygiene product dispenser includes wherein the trigger slides freely between the terminating ends of the slot when the suction cup is at the holding position.

In some embodiments, the feminine hygiene product dispenser includes wherein the linkage includes a lever having a first end, a pivot, and a second end, wherein the lever is rotatably coupled to the lever housing at the pivot, the first end is detached from the trigger, and the second end is operatively connected to a linkage having a suction arm coupled to the suction cup and a delivery arm connected to the delivery tray.

In some embodiments, the feminine hygiene product dispenser includes wherein the suction cup includes a concave surface having a compressed state and an uncompressed state, wherein actuation of the trigger moves the suction cup to the compressed state and into contact with the timing plate where the compressed state holds the suction cup to the plate.

In some embodiments, the feminine hygiene product dispenser further includes an air flow adjuster operatively connected to the timing plate, wherein the air flow adjuster includes a plurality of positions with respect to the timing plate to determine a time period for the suction cup to move from the compressed state to the uncompressed state.

In some embodiments, the feminine hygiene product dispenser includes wherein movement of the suction cup from the compressed state to the uncompressed state adjusts the position of the delivery arm to move the delivery tray from the product delivery position to a product receiving position.

In some embodiments, the feminine hygiene product dispenser includes wherein the suction arm is coupled to the delivery arm by a two bar link.

In another embodiment, there is provided a product dispensing module for dispensing hygiene products. The module includes a suction cup, a delivery tray, and a trigger operatively connected to the suction cup and to the delivery tray. Actuation of the trigger moves the suction cup to a holding position and positions the delivery tray to a product delivery position.

In some embodiments, the product dispensing module further includes a linkage operatively connected to the trigger, to the suction cup, and to the delivery tray, wherein actuation of the trigger moves the linkage to engage the suction cup into contact with a timing plate at the holding position.

In some embodiments, the product dispensing module further includes a trigger plate fixedly coupled to the trigger and to a lever housing, wherein the lever housing supports sliding movement of the trigger plate.

In some embodiments, the product dispensing module includes wherein the trigger plate includes a tab that engages a slot of the lever housing, wherein the slot incudes terminating ends that limit movement of the trigger plate and the trigger.

In some embodiments, the product dispensing module includes wherein the linkage includes a lever having a first end, a pivot, and a second end, wherein the lever is rotatably coupled to the lever housing at the pivot, the first end is detached from the trigger, and the second end is operatively connected to a linkage having a suction arm coupled to the suction cup and a delivery arm connected to the delivery tray.

In some embodiments, the product dispensing module includes wherein the suction cup includes a concave surface having a compressed state and an uncompressed state, wherein actuation of the trigger moves the suction cup to the compressed state and into contact with the timing plate where the compressed state holds the suction cup to the plate.

In some embodiments, the product dispensing module includes wherein the trigger includes a trigger support that is positionable with respect to the lever while the suction cup is in the compressed state to prevent movement of the delivery tray from the product delivery position to a product receiving position.

In a further embodiment, there is provided a method of dispensing a feminine hygiene product from a product dispenser. The method includes: actuating a lever linkage in response to actuation of a trigger, wherein the lever linkage is coupled to a delivery tray and a suction cup; moving the delivery tray to a delivery position while compressing the suction cup to a timing block with actuation of the trigger; preventing movement of the delivery tray to the delivery position with movement of the trigger; and moving the delivery tray to a receiving position with decompression of the suction cup.

In some embodiments, the method includes wherein the preventing movement step includes preventing decompression of the suction cup with movement of the trigger.

In some embodiments, the method further includes preventing decompressing of the suction cup after compressing the suction cup based on an adjustment to a timing block wherein preventing decompressing of the suction cup is based on limiting air flow through the timing block based on a position of a timing screw.

Further novel features and other aspects of the present invention will become apparent from the following detailed description and discussion.

BRIEF DESCRIPTION OF THE DRAWINGS

Referring particularly to the drawings for the purpose of illustration only and not limitation, there is illustrated as follows.

DETAILED DESCRIPTION OF THE EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
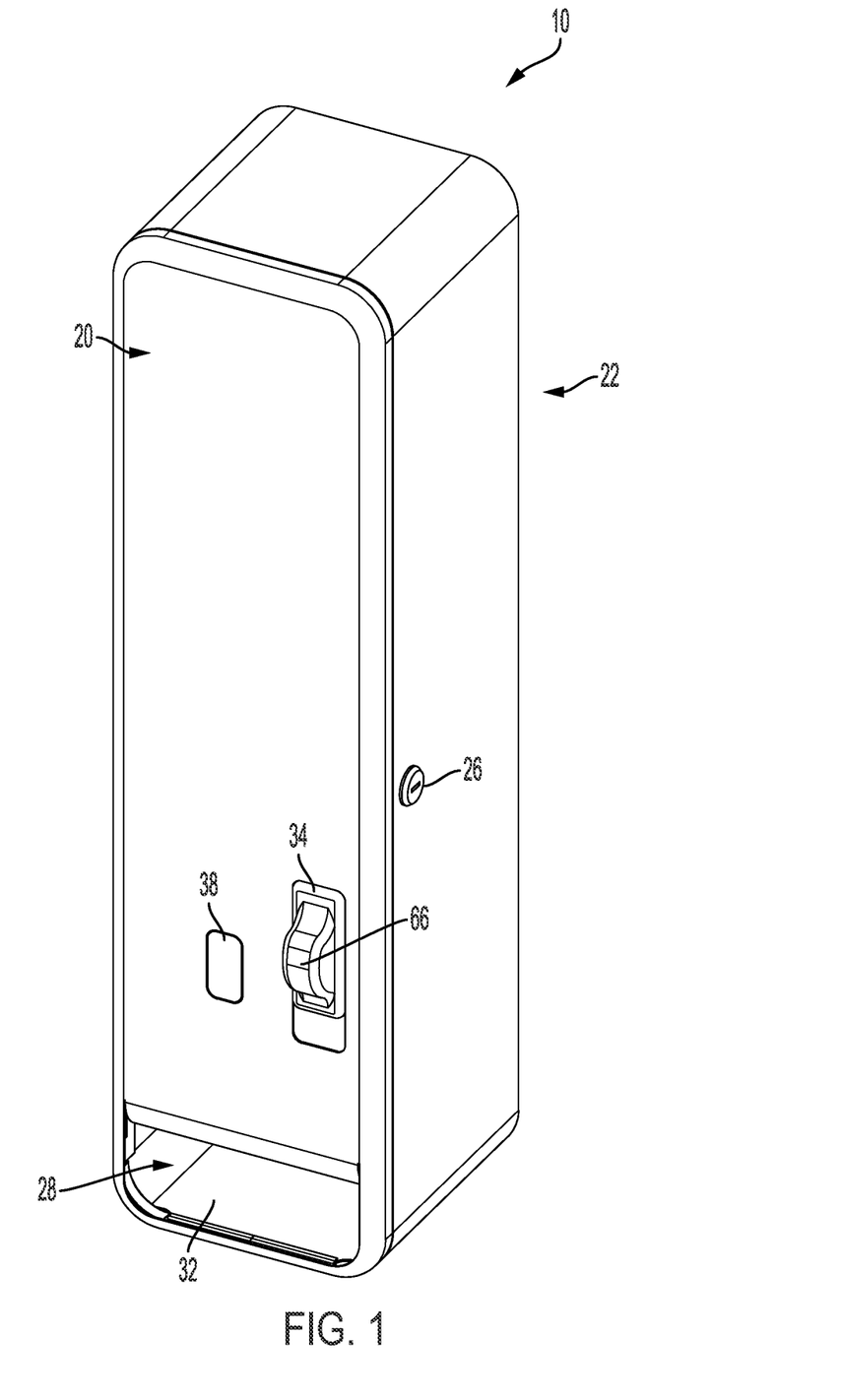
FIG. 1 illustrates an elevational perspective front view of a dispenser apparatus in a closed condition.
Figure 2:
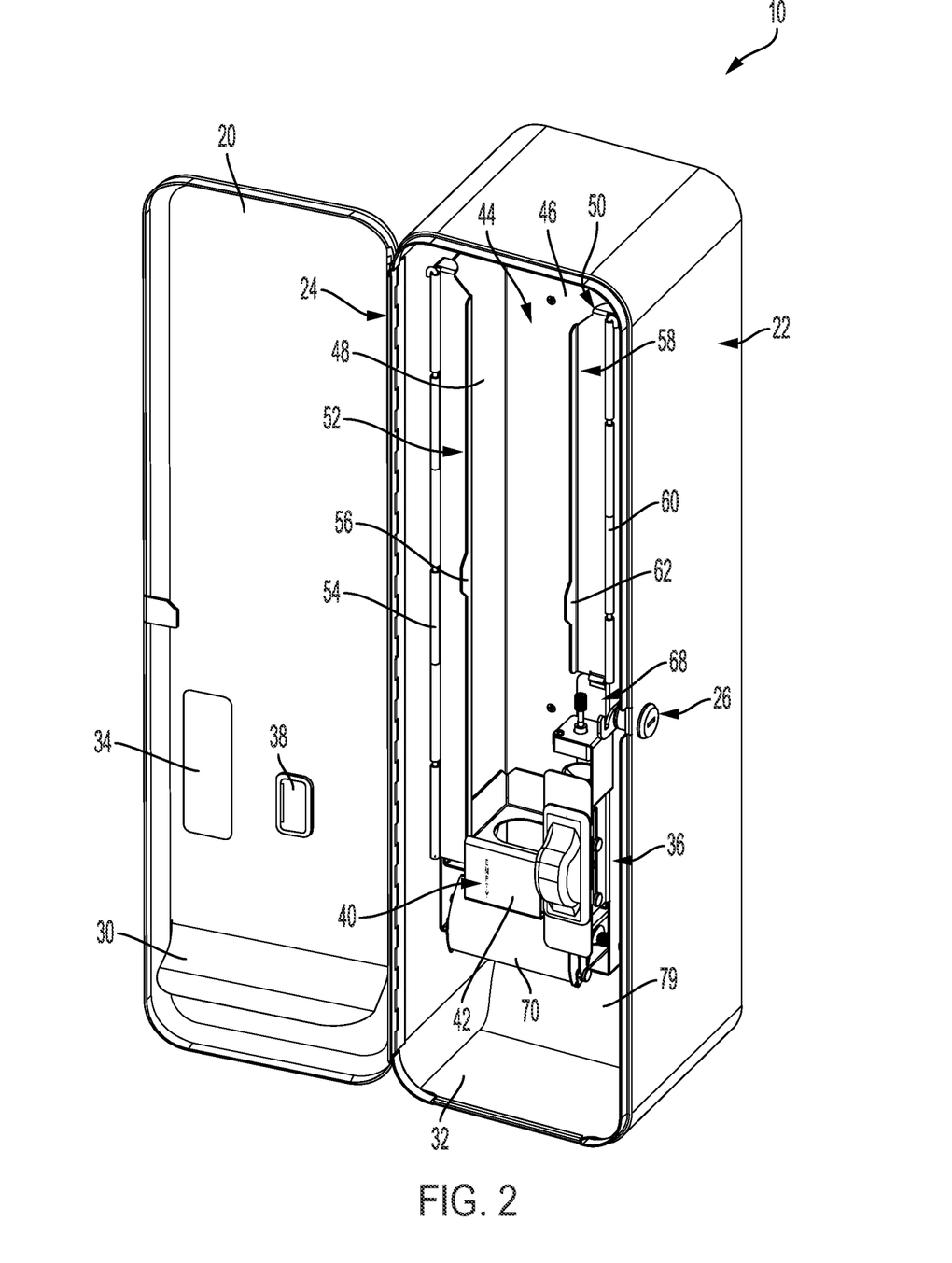
FIG. 2 illustrates an elevational perspective front view of a dispenser with a door in an open position.

FIGS. 1 and 2 illustrates a feminine hygiene product dispensing apparatus 10. The apparatus 10 includes a front door 20 coupled to a cabinet or housing 22. In one embodiment, the housing 22 is a unitary single piece housing. In another embodiment, the housing includes side portion coupled to a separate back wall. The front door 20 is hinged to the housing 22 with a hinge 24 to enable the door 20 to open when a lock 26 is unlocked. In other embodiments, a plurality of locks is included and can be located on the side portions, a top portion, or bottom portion of the housing 22. The front door 20 defines a space 28 with the housing 22 which enables a user to remove a dispensed product from the apparatus 10. A guard 30 (see FIG. 2) is connected to an inside face of the door 20 which substantially prevents an individual from reaching into the apparatus to remove additional products, as opposed to taking products one by one in response to actuation of a trigger assembly 36.

The door 20 includes an opening 34, at which the trigger assembly 36 is located. A window 38 includes a transparent lens which is sufficiently transparent to enable a consumer to see an indicator or mark 40 (see FIG. 2) which indicates that the apparatus 10 is out of hygiene products and requires filling. In this embodiment, the word "Empty" is located on a face of a weight 42. In one embodiment, the dispenser dispenses a product without requiring a payment or any other compensation, wherein the products are provided as a courtesy. In other embodiments, compensation is required including, coins, bills, credit cards, debit cards, and cryptocurrency.

A dispensing module 44, also identified as a rack, includes a back wall 46, a first side wall 48 and a second side wall 50. The rack 44 is configured to hold a stack of hygiene products (not shown) which are arranged in a column. In one embodiment, the hygiene products are feminine hygiene pads, also known as sanitary pads, that includes sides that are rectangular and typically having a height that is less than a width or length. Other products having other dimensions are contemplated. The products are stacked one upon another and the weight is placed on the product located at the top of the stack. The weight compress the stack to insure proper dispensing and also includes the indicator.

A first module door 52 is coupled to the first side wall 48 by a first hinge 54 and includes a tab 56 to enable a user or maintenance person to open and close the door 52. A second module door 58 is coupled to the second sidewall 50 by a second hinge 60 and includes a tab 62. Each of the first module door 52 and the second module door 58 include open and closed positions. In the open positon, the doors 52 and 58 enable bulk loading of the hygiene products. In the closed positions, the doors 52 and 58 maintain alignment of the product as a stack within the rack 44. The tabs 56 and 62 provide a location to help a maintenance person or user to more readily open and close the doors 52 and 58.

Figure 3:
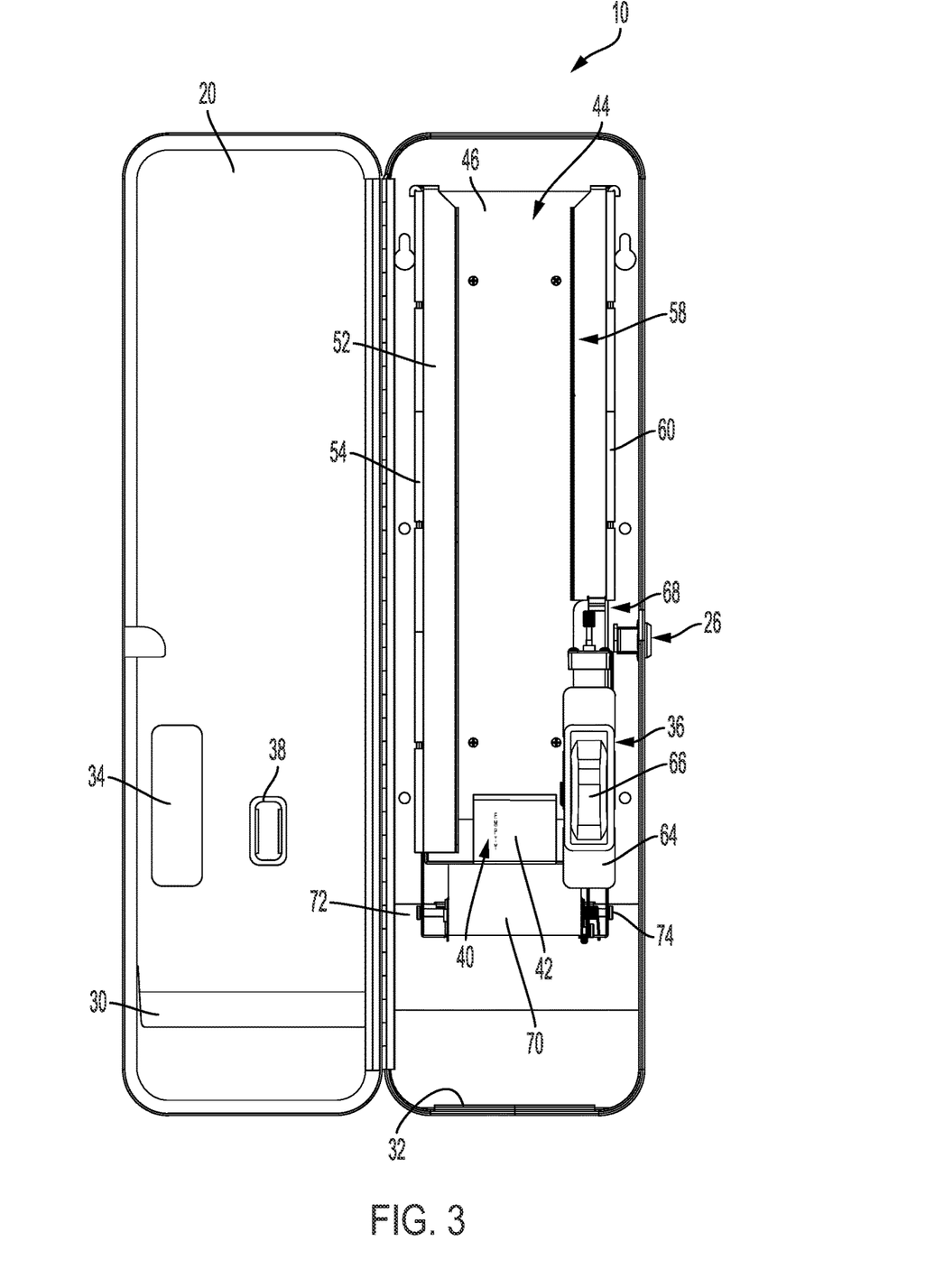
FIG. 3 illustrates an elevational front view of a dispenser with a door in an open position.

FIG. 3 illustrates a front elevational view of the apparatus 10 with the door 20 in the open position. The trigger assembly 36 includes a trigger plate 64 and a trigger cover 66, the parts of which either collectively or individually are generally considered as a trigger. The trigger cover 66 slides vertically, as illustrated, with the trigger plate 64 to which it is attached. The trigger assembly 36 includes a timing assembly 68 which adjusts the time between dispensing a first product and as second product, as later described herein. A delivery tray 70, located below the sidewalls of the module 44 and the stack of hygiene products, receives a single product from the stack of products and dispenses the single product from the shelf 32. The delivery tray 70 rotates about a first pivot 72 and a second pivot 74. Actuation of the trigger cover 66 actuates dispensing of the product when moved in an upward or vertical position.

Figure 4:
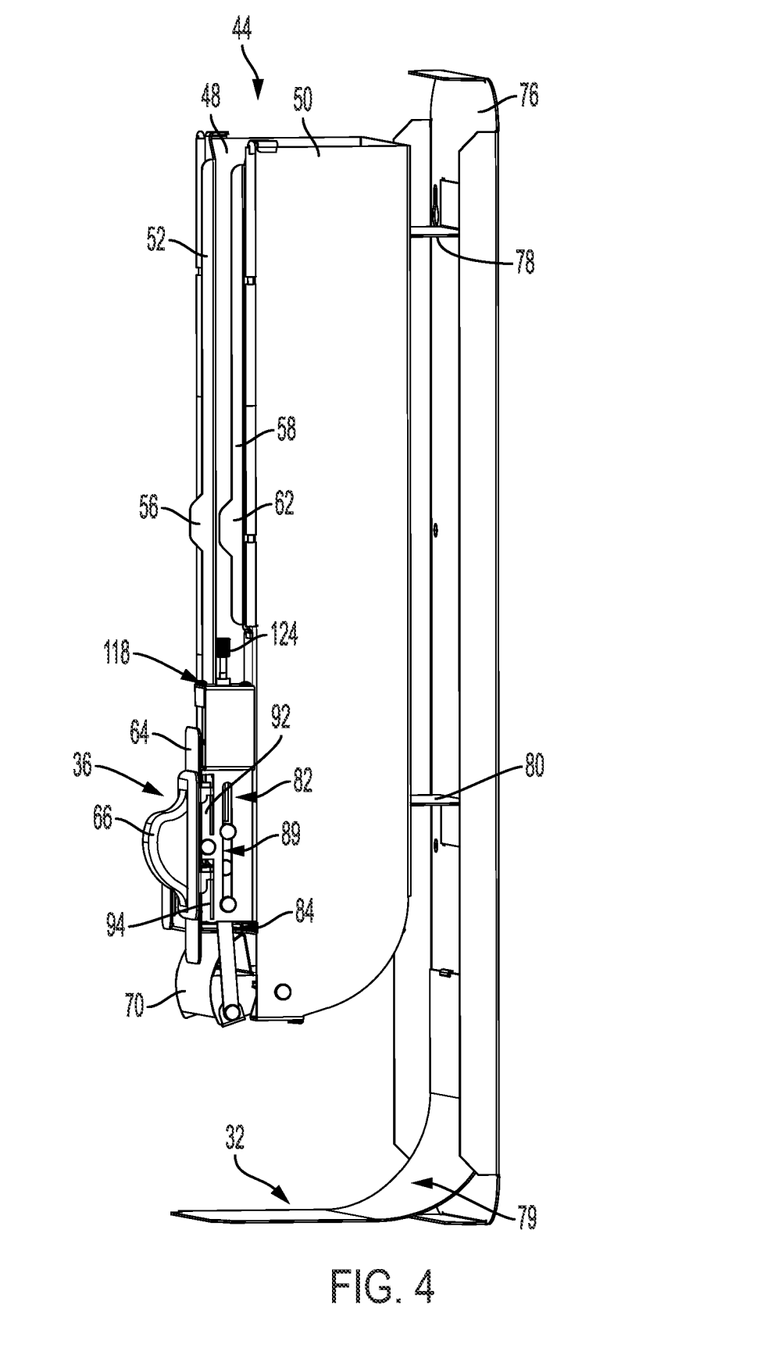
FIG. 4 illustrates an elevational perspective view of a dispensing module coupled to a back wall.

As seen in FIG. 4, the module 44 is connected to a back wall 76 of the housing 22 with a first bracket 78 and second bracket 80. Other types of support structures coupling the module 44 to the back wall 76 are contemplated. The module 44, in different embodiments, is assembled as a complete package for installation in the housing 22. The module 44 includes the trigger assembly 36 and the delivery tray 70. During delivery of the product, the delivery tray 70 directs the released product toward a ramp 79 and onto the shelf 32. The ramp 79 directs the product to the shelf 32 when the product is dispensed.

Figure 5:
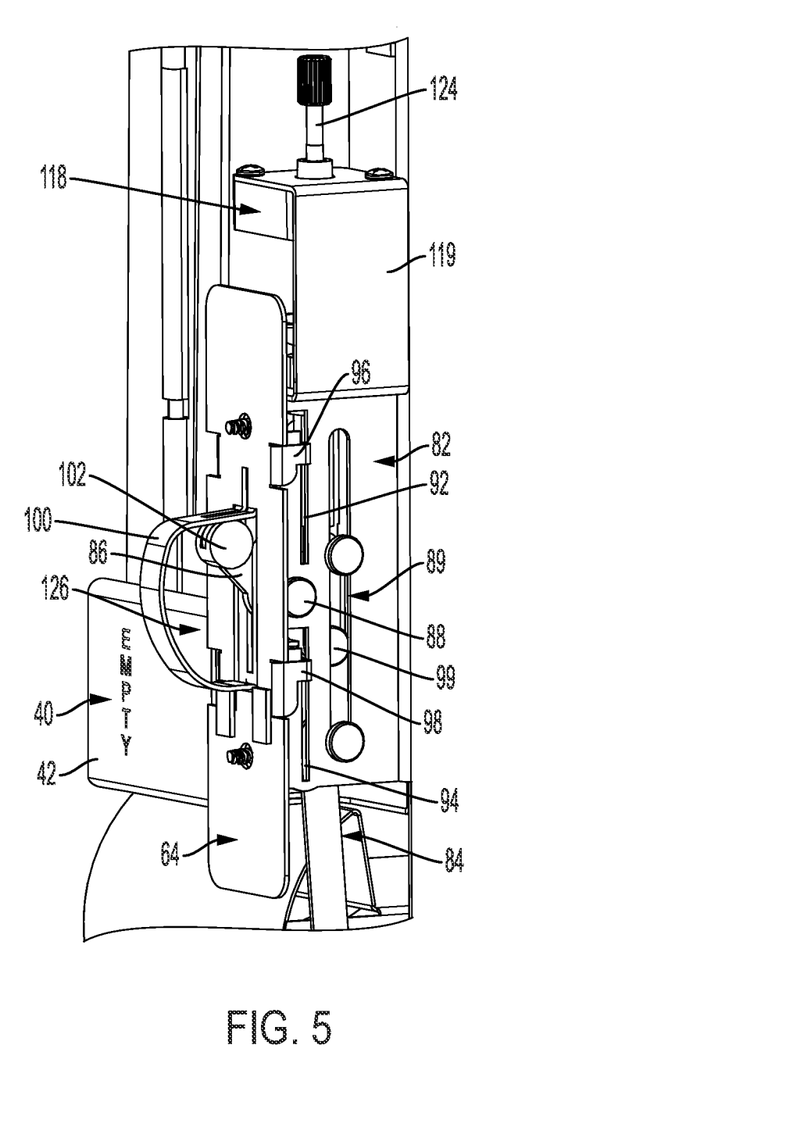
FIG. 5 illustrates a portion of a dispensing module.
Figure 6:
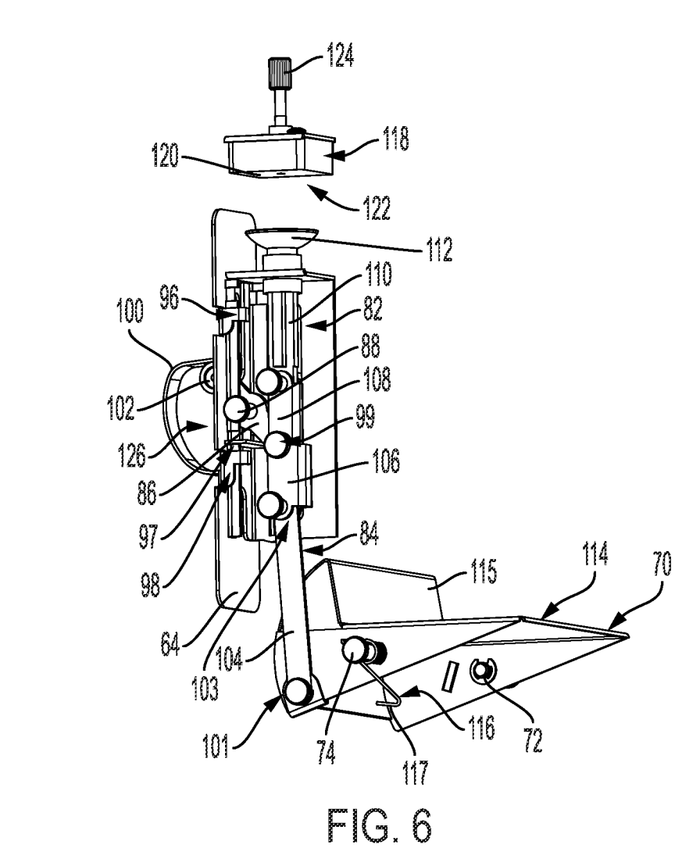
FIG. 6 illustrates a trigger assembly coupled to a delivery tray in a first position.
Figure 7:
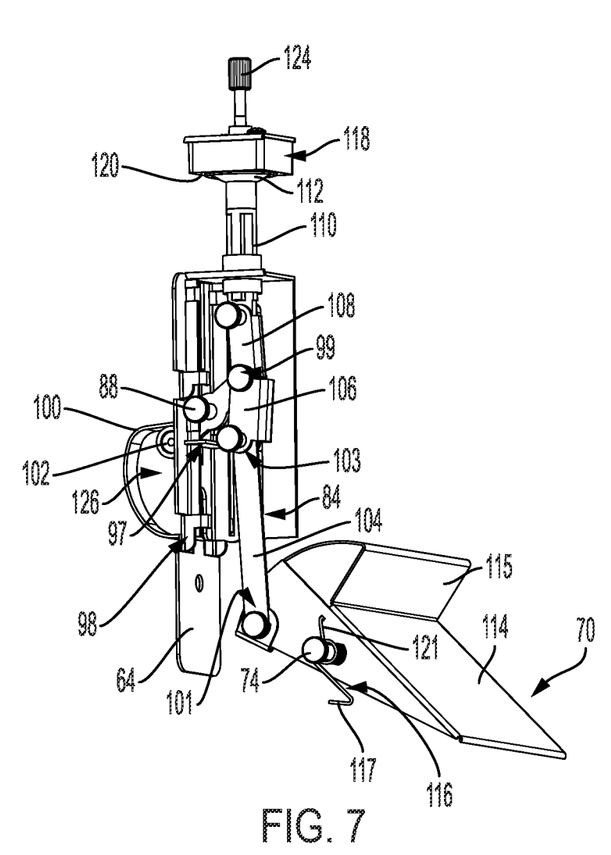
FIG. 7 illustrates a trigger assembly coupled to a delivery tray in a second position.

The trigger assembly 36 includes a trigger housing 82 that supports a lever linkage 84 that includes a lever 86 that pivots about a pivot 88 as illustrated in FIGS. 5, 6, and 7. In addition, the trigger housing 82 includes a lever slot 89 to support movement of the lever linkage 84. The trigger housing 82 also includes a first trigger slot 92 and a second trigger slot 94. Trigger tabs 96 and 98 that extend from the trigger plate 64, engage the first and second trigger slots 92, 94 to provide for vertical sliding movement of the trigger plate 64. As the trigger cover 66 is moved in either vertical direction, a trigger support 100 moves the trigger plate 64 vertically. While only one side of the trigger housing 92 is shown, the trigger housing 92 includes a second side similarly configured as the illustrated side of FIG. 5 to support movement of the lever linkage 84 and sliding movement of the trigger tabs 96 and 98. In some embodiments, the trigger plate 64, the trigger cover 66, and the trigger support 100, are a unitary one piece assembly or are a two piece assembly.

Movement of the trigger support 100 in a downward direction, contacts a first end 102 of the lever 86. The first end 102 is detached from the trigger support 100. As the first end 102 moves downwardly, the trigger plate 64, including trigger tabs 96, also moves downwardly, and a second end 99 of the lever 86 moves upwardly. The lever 86 pivots about the pivot 88 to actuate movement of the lever linkage 84 and the delivery tray 70. The lever linkage 84, as seen in FIGS. 6 and 7, includes a delivery arm 104 having a first end 101 rotatably coupled to the delivery tray 70 and a second end 103 rotatably coupled to a first lever arm 106 which is in turn coupled a second lever arm 108. The first lever arm 106 and the second lever arm 108 are a two bar link that enables the lever 86 to move the position of the tray 70 from a receiving position to the delivery position and vice versa. Because the lever 86 pivots about the pivot 88, the end 99 of the lever 86 moves in a non-linear direction, i.e. an arc. Since the end 99 is coupled to the two bar link where the first lever arm 106 and the second lever arm 108 connect, movement of the lever linkage 84 moves in the vertical direction without being restricted. This configuration provides a smooth vertical operation which substantially prevents jamming of the linkage 84. The second lever arm 108 is further coupled to a suction cup arm 110 which is connected to a suction cup 112. The suction cup includes a concave surface which includes a compressed state and an uncompressed state. One side of the trigger housing 82 is not shown in FIGS. 6 and 7 to illustrate the parts of the lever linkage 84 supported by the trigger housing 82.

The delivery tray 70 includes a planar support 114, upon which a bottom hygiene product from the stack of hygiene products, is located for dispensing. The delivery tray 70 of FIG. 6 is in the receiving position. The delivery tray 70 also includes a back support 115 that extends upwardly from the planar support 114. The first end 101 of the delivery arm 104 is rotatably coupled to the delivery tray 70 and upon actuation of the trigger support 100, the delivery tray 70 rotates about pivots 72 and 74 of FIG. 3. As the trigger support 100 moves downward, the linkage 84 moves upwardly and the delivery tray rotates in a clockwise position about pivots 72 and 74 to the delivery position of FIG. 7. A spring 116, coupled to the pivot 72, includes a first end 117 coupled to the body of the module 44, such as the second side wall 50, which resists rotational movement of the delivery tray 70 from a receiving position of FIG. 6 to the delivery positon of FIG. 7. A second end 121 of the spring 116 maintains tension in the spring 116 when the tray 70 is in the delivery position.

As the trigger support 100 is moved downward, the suction cup arm 110 and the suction cup 112 are moved in an upward direction toward a timing block 118 that includes a timing plate 120 having an aperture 122. The timing block 118 is fixed in place by a block support 119. The timing block 118 further includes sidewalls and a top wall defining an air chamber with the timing plate 120. The length of suction cup arm 110 is selected such that movement of the lever linkage 84 moves the suction cup 112 into contact with the timing plate 120 to compress the suction cup 112. When compressed, the suction cup 112 is in a state of compression at a holding position and provides a temporary vacuum. Compression of the suction cup 112 causes the delivery tray 70 to be held in the delivery position for a period of time until the suction cup decompresses to a decompression state, which returns the delivery tray 70 to the receiving position of FIG. 6 as a result of spring 74 releasing tension.

The period of time in which the delivery tray 70 is held in the delivery position is determined, at least in part, by an air flow screw 124 rotatably coupled to the timing block 118. Rotational adjustment of the screw 124 adjusts the amount of time the suction cup 112 remains in the compressed state before returning to the uncompressed state. The air flow screw 124 adjusts the amount of air leaking or moving into the timing block. Other types of air flow adjusters are contemplated such as a sliding mechanism. In another embodiment, the air flow screw 124 is coupled to the timing block at a different location. Additionally, the tension of the spring 116 determines with the positon of the screw 124, the time of which the suction cup 112 remains in the compressed state. Upon release of the suction cup 112 from the timing plate 120, the lever 86 moves to the position of FIGS. 5 and 6.

As seen in FIGS. 5, 6, and 7, the trigger support 100 defines an interior space 126 between the trigger support 100 and the trigger plate 64. The first end 102 of the lever 86 is located in the interior space 126. As the trigger support 100 is moved to a downward position, the first end 102, due to its contact with the trigger support 100, moves downwardly as well. Once the trigger support 100 reaches its position of FIG. 7, the trigger support 100 remains in contact with the first end 102 as long as the trigger support is not moved upwardly by an applied force. Typically this applied upward force results from a user moving the trigger cover 66 in an upward direction. Because the trigger plate 64 is slidably connected to the slots 92 and 94, the trigger plate 64 is freely movable in an upward direction dues to the size of the interior cavity 126. Upward movement of the trigger plate 64 is limited by contact of the tab 98 with a trigger stop 97. As seen in FIGS. 6 and 7, the trigger stop 97 is a generally horizontal plate which is contacted by the tab 98, if the trigger support 100 is moved in an upward direction. Other types of stops are contemplated. Additionally, the trigger stop 97 prevents removal of the trigger without the removal of additional parts. This limited movement of the trigger plate 64 prevents the first end 102 of the lever 86 from being moved upwardly while the suction cup 112 is in the compressed state. Consequently, the suction cup 112 cannot be displaced from contact with the timing plate 120 by a user. This inability to move the suction cup 112 from the timing plate, prevents the user from dispensing additional hygiene products before the delay provided by the compress suction cup has elapsed. The delay, therefore, provides a measure of protection to prevent an individual from taking more feminine hygiene products than is necessary, or even from emptying the dispenser 10. The delay also acts as a reminder to a user to dispense only what is needed and that other individuals will require feminine hygiene products for their personal use.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A feminine hygiene product dispenser comprising:
   a rack to hold a plurality of feminine hygiene products;
   a weight adapted to fit within the rack, wherein the weight is supported by a last feminine hygiene product to be dispensed from the rack, the weight including an indicator;
   a housing including a door, wherein the door includes a window through which the indicator appears in the absence the plurality of feminine hygiene products; and
   a product dispensing module including a suction cup having a compressed state and an uncompressed state, a delivery tray, and a trigger including a trigger support extending through an opening of the door, the trigger support configured to be moved vertically by a user, the trigger support defining an interior space having a lever disposed within the interior space, wherein the lever is operatively connected to the suction cup and to the delivery tray, wherein actuation of the trigger support in a downward direction by the user moves the lever about a pivot to move the suction cup in an upward direction to a holding position in which the suction cup is compressed in the compressed state, and to position the delivery tray to a product delivery position, wherein the delivery tray is held at the product delivery position until the suction cup decompresses to the uncompressed state to return the delivery tray to a product receiving position, wherein movement of the trigger support in the upward direction when the suction cup is in the compressed state does not displace the suction cup from the holding position.

2. The feminine hygiene product dispenser of claim 1 further comprising a linkage operatively connected to the trigger, to the suction cup, and to the delivery tray, wherein actuation of the trigger in the downward direction moves the linkage to move the suction cup in the upward direction and to engage the suction cup into contact with a timing plate at the holding position.

3. The feminine hygiene product dispenser of claim 2 further comprising a trigger plate fixedly coupled to the trigger support and to a lever housing, wherein the lever housing supports vertical sliding movement of the trigger plate.

4. The feminine hygiene product dispenser of claim 3 wherein the trigger plate includes a tab that engages a slot of the lever housing, wherein the slot incudes terminating ends that limit movement of the trigger plate and the trigger support.

5. The feminine hygiene product dispenser of claim 4 wherein the trigger support slides freely in a vertical direction between the terminating ends of the slot when the suction cup is at the holding position.

6. The feminine hygiene product dispenser of claim 5 wherein the linkage includes lever having a first end, a pivot, and a second end, wherein the lever is rotatably coupled to the lever housing at the pivot, the first end is detached from the trigger support, and the second end is operatively connected to a linkage having a suction arm coupled to the suction cup and a delivery arm connected to the delivery tray.

7. The feminine hygiene product dispenser of claim 6 wherein the suction cup includes a concave surface having the compressed state and the uncompressed state, wherein actuation of the trigger moves the suction cup to the compressed state and into contact with the timing plate where the compressed state holds the suction cup to the timing plate.

8. The feminine hygiene product dispenser of claim 7 further comprising an air flow adjuster operatively connected to the timing plate, wherein the air flow adjuster includes a plurality of positions with respect to the timing plate to determine a time period for the suction cup to move from the compressed state to the uncompressed state.

9. The feminine hygiene product dispenser of claim 8 wherein movement of the suction cup from the compressed state to the uncompressed state adjusts the position of the delivery arm to move the delivery tray from the product delivery position to a product receiving position.

10. The feminine hygiene product dispenser of claim 9 wherein the suction arm is coupled to the delivery arm by a two bar link.

11. A product dispensing module for dispensing hygiene products comprising:
    a suction cup having a compressed state and a uncompressed state;
    a delivery tray; and
    a trigger including a trigger support defining an interior space and a lever disposed within the interior space, wherein the lever is operatively connected to the suction cup and to the delivery tray, wherein actuation of the trigger support moves a first end of the lever in a downward direction which moves the suction cup in an upward direction to the compressed state at a holding position and positions the delivery tray to a product delivery position, wherein the holding position prevents movement of the trigger support from dispensing one of the hygiene products until the suction cup decompresses to the uncompressed state, and wherein movement of the trigger in an upward direction when the suction cup is in the holding position prevents the user from dispensing additional hygiene product until a delay provided by the compressed state of the suction cup has elapsed.

12. The product dispensing module of claim 11 further comprising a linkage operatively connected to the trigger, to the suction cup, and to the delivery tray, wherein actuation of the trigger moves the linkage to engage the suction cup into contact with a timing plate at the holding position.

13. The product dispensing module of claim 12 further comprising a trigger plate fixedly coupled to the trigger and to a lever housing, wherein the lever housing supports sliding movement of the trigger plate in a vertical direction.

14. The product dispensing module of claim 13 wherein the trigger plate includes a tab that engages a slot of the lever housing, wherein the slot incudes terminating ends that limit movement of the trigger plate and the trigger.

15. The product dispensing module of claim 14 wherein the linkage includes the lever having the first end, a pivot, and a second end, wherein the lever is rotatably coupled to the lever housing at the pivot, the first end is detached from the trigger support, and the second end is operatively connected to a linkage having a suction arm coupled to the suction cup and a delivery arm connected to the delivery tray.

16. The product dispensing module of claim 15 wherein the suction cup includes a concave surface having the compressed state and the uncompressed state, wherein actuation of the trigger moves the suction cup in the upward direction to the compressed state and into contact with the timing plate where the compressed state holds the suction cup to the plate.

17. The product dispensing module of claim 16 wherein the trigger support is positionable in the upward direction with respect to the lever while the suction cup is in the compressed state to prevent movement of the delivery tray from the product delivery position to a product receiving position.

18. A method of dispensing a feminine hygiene product from a product dispenser comprising:
   actuating a lever linkage in response to actuation of a trigger in a vertical direction, wherein the lever linkage is coupled to a delivery tray and a suction cup;
   moving the delivery tray to a delivery position to deliver a first feminine hygiene product to a user while moving the suction cup in an upward direction to a compressed state by compressing the suction cup to a timing block with actuation of the trigger in the vertical direction;
   preventing movement of the delivery tray to the delivery position with vertical movement of the trigger while the suction cup is in the compressed state, wherein vertical movement of the trigger while the suction cup is in the compressed state does not move the suction cup from the compressed state and prevents the user from dispensing another feminine hygiene product; and
   moving the delivery tray to a receiving position with decompression of the suction cup.

19. The method of claim 18 wherein the preventing movement step includes preventing decompression of the suction cup with vertical movement of the trigger.

20. The method of claim 19 further comprising preventing decompressing of the suction cup after compressing the suction cup based on an adjustment to a timing block wherein preventing decompressing of the suction cup is based on limiting air flow through the timing block based on a position of a timing screw.

* * * * *